United States Patent
Ehlbeck et al.

(10) Patent No.: US 9,855,355 B2
(45) Date of Patent: Jan. 2, 2018

(54) METHOD AND DEVICE FOR PLASMA-TREATING HOLLOW BODIES

(71) Applicant: INP GREIFSWALD—LEIBNIZ-INSTITUT FÜR PLASMAFORSCHUNG UND TECHNOLOGIE E. V., Greifswald (DE)

(72) Inventors: Joerg Ehlbeck, Hinrichshagen (DE); Manfred Stieber, Greifswald (DE); Klaus-Dieter Weltmann, Binz (DE)

(73) Assignee: INP GREIFSWALD—LEIBNIZ-INSTITUT FÜR PLASMAFORSCHUNG UND TECHNOLOGIE E.V., Greifswald (DE)

( * ) Notice: Subject to any disclaimer, the term of this patent is extended or adjusted under 35 U.S.C. 154(b) by 0 days.

(21) Appl. No.: 14/772,385

(22) PCT Filed: Mar. 4, 2014

(86) PCT No.: PCT/EP2014/054166
§ 371 (c)(1),
(2) Date: Sep. 3, 2015

(87) PCT Pub. No.: WO2014/135531
PCT Pub. Date: Sep. 12, 2014

(65) Prior Publication Data
US 2016/0008500 A1    Jan. 14, 2016

(30) Foreign Application Priority Data
Mar. 4, 2013 (DE) .......... 10 2013 203 648

(51) Int. Cl.
*A61L 2/14* (2006.01)

(52) U.S. Cl.
CPC ........... *A61L 2/14* (2013.01); *A61L 2202/121* (2013.01); *A61L 2202/122* (2013.01); *A61L 2202/23* (2013.01)

(58) Field of Classification Search
None
See application file for complete search history.

(56) References Cited

U.S. PATENT DOCUMENTS

| | | | | | |
|---|---|---|---|---|---|
| 4,221,972 | A | * | 9/1980 | Oppel | C21D 1/38 219/780 |
| 5,216,223 | A | * | 6/1993 | Straemke | C23C 16/54 118/719 |

(Continued)

FOREIGN PATENT DOCUMENTS

| | | |
|---|---|---|
| DE | 19807742 | 10/1999 |
| DE | 19916479 | 10/2000 |

(Continued)

OTHER PUBLICATIONS

Searcht report issued for Priority Application—German Patent Application No. 10 2013 203 648.5, dated Aug. 7, 2014.

*Primary Examiner* — Kishor Mayekar
(74) *Attorney, Agent, or Firm* — Soroker Agmon Nordman

(57) ABSTRACT

An essential feature of the invention is the original combination of a plasma process and a sealing system. This is achieved with external tubes (4, 6), which are connected to each other so as to be impermeable to gas, but galvanically insulated, and of which at least one is electrically conductive, such that the external tubes form an antechamber between the two external tubes (4, 6) and a treatment chamber between the external tube (6) and the internal tube (1).

9 Claims, 4 Drawing Sheets

(56) References Cited

U.S. PATENT DOCUMENTS 5,897,831 A * 4/1999 Jacob .................. A61L 2/14
                                                    204/164
7,914,692 B2 * 3/2011 Saito ................ H01J 37/32027
                                                 204/192.12

FOREIGN PATENT DOCUMENTS

DE   102008034111   1/2010
EP       2008670   12/2008

* cited by examiner

Carrier beam with gas supply and electrical power supply as well as lateral seating for transport chains Tool magazine Tool changing station Treatment area

METHOD AND DEVICE FOR PLASMA-TREATING HOLLOW BODIES

DESCRIPTION OF THE INVENTION

The present invention relates to a device for plasma-treating hollow bodies, such as bottles, vials, syringes, shut-off caps, etc., in particular with a view to sterilising said hollow bodies, and is equally suitable for various discharge types such as dielectric barrier discharge and discharges with high frequency and microwave excitation. The core of the invention is a system consisting of three, preferably concentrically arranged, tubes (shells), wherein the inner shell serves as an internal conductor or respectively internal electrode, the middle shell represents the—sealed partially on the base plate—external conductor or respectively external electrode and the outer shell has a seal on the top end. The device allows a pressure gradient to be set between the interior and the exterior of the object to be treated, which can be advantageously used for process control and plasma formation and forms the basis for an optimised in-line method of plasma treatment of hollow bodies.

STATE OF THE ART

In particular in the pharmaceutical industry, there is a high demand for high-rate sterilisation methods for primarily small hollow bodies in the range of 2 to 100 ml. Typical examples of these are vials and syringes.

There is an increasing desire to replace classic thermal methods, although they have proven to be very safe methods, with modern methods. The anticipated main advantages are shorter process times, in particular the avoidance of cooling buffers, and the accompanying, more compact structure, or respectively a higher throughput with the same construction volume.

Methods of gas sterilisation, such as the use of ethylene oxide, formaldehyde or hydrogen peroxide, are problematic in their application and bear the risk of a negative interaction with the pharmaceutical preparation to be filled. Even plasma-based indirect methods like ozonation or the PPA method, which minimize risk of damage, are subject to this interaction risk.

Direct plasma methods at atmospheric pressure, such as the use of high-frequency-excited plasma jets, fail in noble gas mode at the operating costs caused by the high gas consumption. During transition to air mode, if technically implementable, the service life drops on one hand and the gas temperature increases so that suitability for thermolabile materials is questionable.

Another example of cold plasmas at atmospheric pressure is the DBE, which would however have to realize great clearances due to the shape of the hollow body. The high voltages required for this make an industrial application difficult.

Low-pressure reactors cause high investment costs through complex and—especially in the case of batch mode—large receptacles with high dead volumes. The pump rates required at high throughput rates are another cost factor for investment and operation.

The publications DE 199 16 479 A1 and DE 10 2008 034 111 A1 also belong to the state of the art. DE 199 16 479 A1 discloses a device for sterilising receptacles by means of plasma at a low pressure. The described plasma concerns a high-frequency plasma. An atmospheric pressure plasma or a dielectric barrier discharge is not described therein. A sealing system, based on a preferably concentrically arranged double chamber, is also not subject matter of DE 199 16 479 A1.

The publication DE 10 2008 034 111 A1 describes a device for sterilising and/or disinfecting workpieces made of plastic, preferably closing caps under atmospheric pressure by means of a plasma. Thus, a special type of a double-chamber system for generating high process gas purity is also not covered in this document.

None of the known technical solutions discloses an efficient cost-saving solution for generating defined process gas atmospheres in high-rate processes. These are essential for achieving stable process conditions. The smallest impurities can—in particular in the case of sterilization processes—lead to complete process failure.

The plasma generation methods listed in the named documents have already been the state of the art for years.

Object of the Invention

The object of the invention is to eliminate the disadvantages of the solutions described in the state of the art.

Solution of the Object

The object was solved by a device for plasma-treating hollow bodies and a corresponding method. An important characteristic of the invention is the first-time combination of the plasma process and sealing system. This is realized such that external tubes (4, 6), of which at least one is electrically conductive, are connected to each other so as to be impermeable to gas, but galvanically insulated such that they form an antechamber between the two external tubes (4, 6) and a treatment chamber between the external tube (6) and the internal tube (1).

BRIEF DESCRIPTION OF THE DRAWINGS

Some non-limiting exemplary embodiments or features of the disclosed subject matter are illustrated in the following drawings.

In the drawings.

DESCRIPTION OF THE INVENTION

Figure 1:
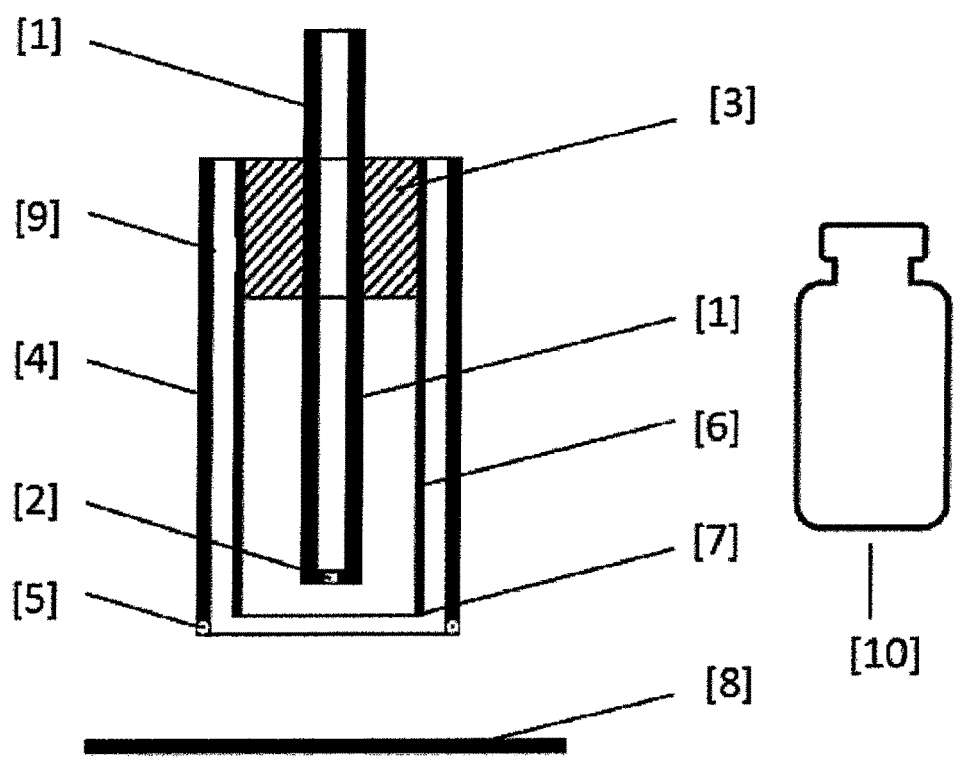
FIG. 1 is a schematic illustration of a device for plasma treating hollow bodies, according to some embodiments of the present disclosure.

The present invention is suitable for different discharge types like DBD, high-frequency and microwave excitation. It describes a system of three preferably concentrically arranged tubes (shells). The internal tube serves as internal conductor or respectively internal electrode, and the middle tube represents the external conductor or the external electrode. It seals partially on the metallic transport plate. The external shell has a seal on the top end. The goal is to direct the gas supply with slight overpressure through the gap between the external and middle shell. Leaks in the sealing system do not thereby lead to a contamination of the process gases. Gas flow and operating pressure can be set via the impermeability of the contact surface of the middle shell to the transport plate. The free selection of the process gas as well as the reduction in the operating pressure make it possible to also operate using DBD vials with their typical shape with moderate voltages. A rough centring of the vials on the device can take place through the lowering process. The fine adjustment can take place in the lowered mode through injection of a not necessarily sterile tangential gas flow. The individual device can be combined into corresponding beams. These can be moved along in parallel with the transport of the vials through transport chains on both sides. By means of the tool change, the system can be adjusted for greatly differing variables. For this, a tool changing station and a tool magazine can be installed on the side facing the treatment location in order to thus perform a fully automated tool change.

The following main problems are thus solved by the invention:
1. No use of complex vacuum reactors
2. Minimization of dead volume, resulting in a reduction in pump performance
3. The sealing problem is solved by the special gas supply
4. Because of use in low to medium pressure, a broad bandwidth of process gasses can be used (e.g. air, noble gases, forming gas, addition of moisture . . . )
5. Form tolerance is given Compared to frequently used batch processes, one has the advantages of an in-line method. In addition, there is the advantage that the volume to be evacuated was minimized in the device, which leads on one hand to lower costs with respect to the evacuation process and minimizes the overall process times. Furthermore, the quantities of required process gases, in particular precursors during coating, are also reduced.

The advantage compared to classic in-line plasma processes is above all the reduced effort for the sealing system. Another important advantage is the increased process safety in the event of a failure of the sealing system.

EXEMPLARY EMBODIMENTS

The invention is explained in greater detail below based on a few examples without restricting the invention to these examples. FIGS. 1, 2, 3, 4 and 5 show the device according to the invention.

The following reference numbers are used for the below drawings:
[1] Electrically conductive internal tube (high-voltage electrode, suctioning)
[2] Openings in the internal tube
[3] Galvanic insulation through a flange
[4] External tube I
[5] Seal
[6] External tube II (earth electrode)
[7] Contact seal
[8] Base plate/floor plate/transport plate
[9] Opening for the supply of the working gas
[10] Object to be treated (hollow body)

Figure 2:
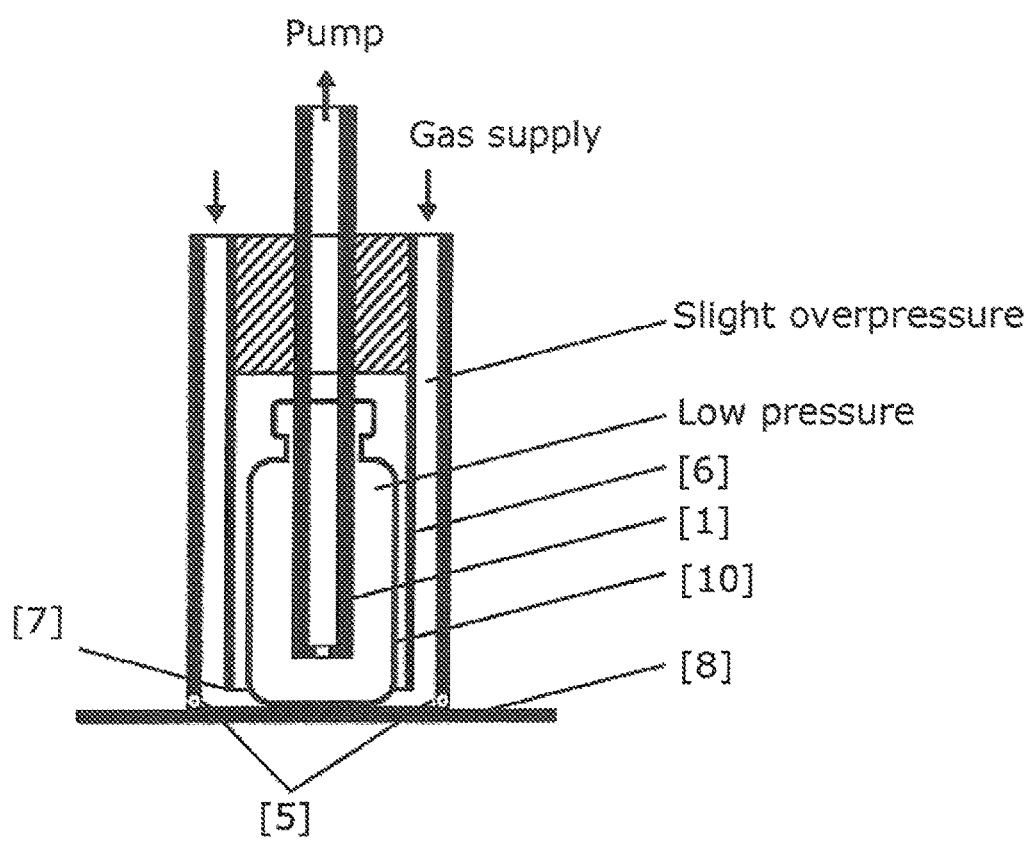
FIG. 2 and FIG. 3 are schematic illustrations of using the device with an object, according to some embodiments of the present disclosure.
Figure 3:
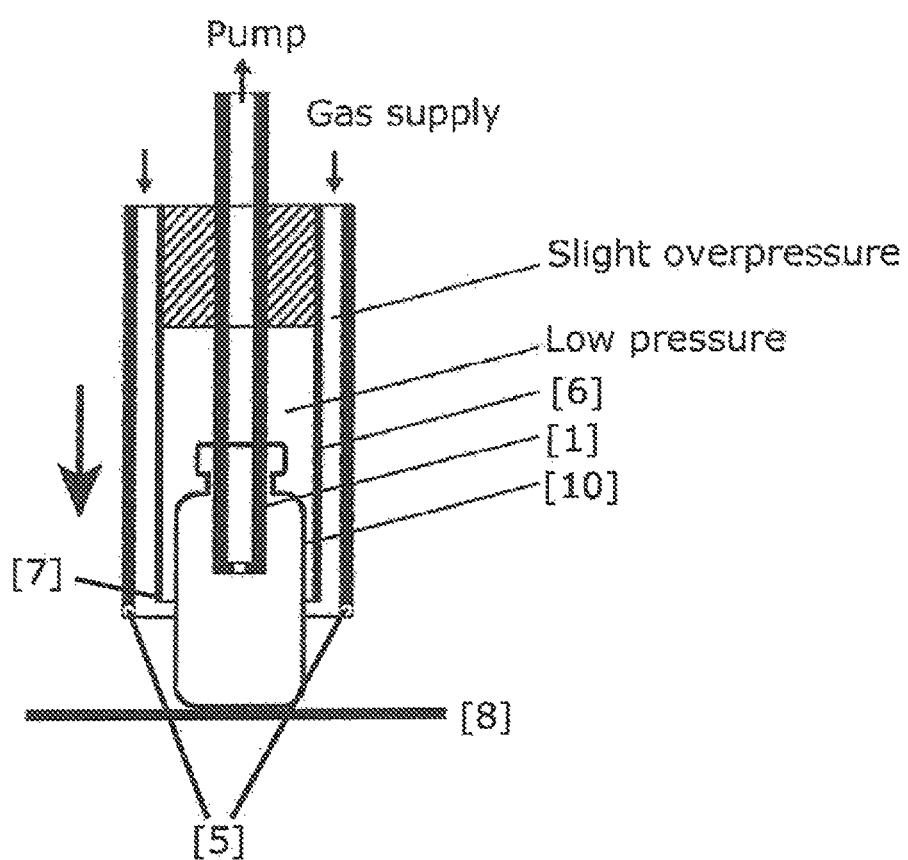
Figure 4:
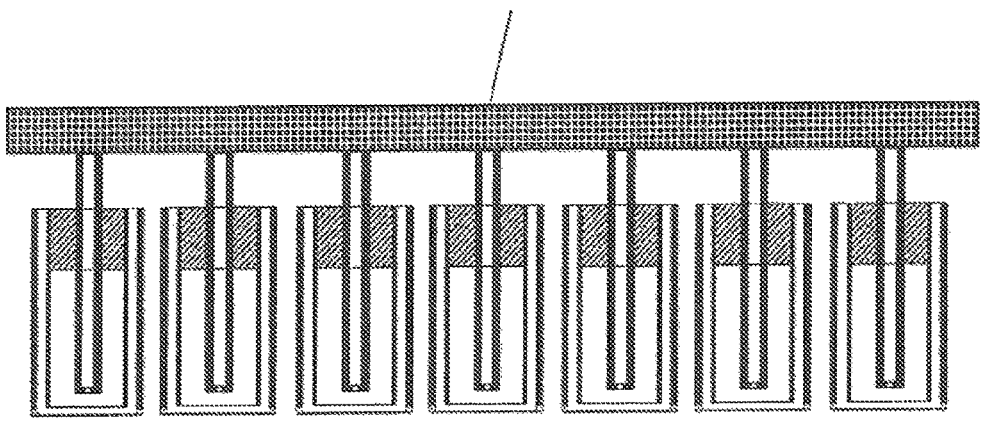
FIG. 4 and FIG. 5 are schematic illustrations of exemplary usage of the device connected to a gas, according to some embodiments of the present disclosure.
Figure 5:
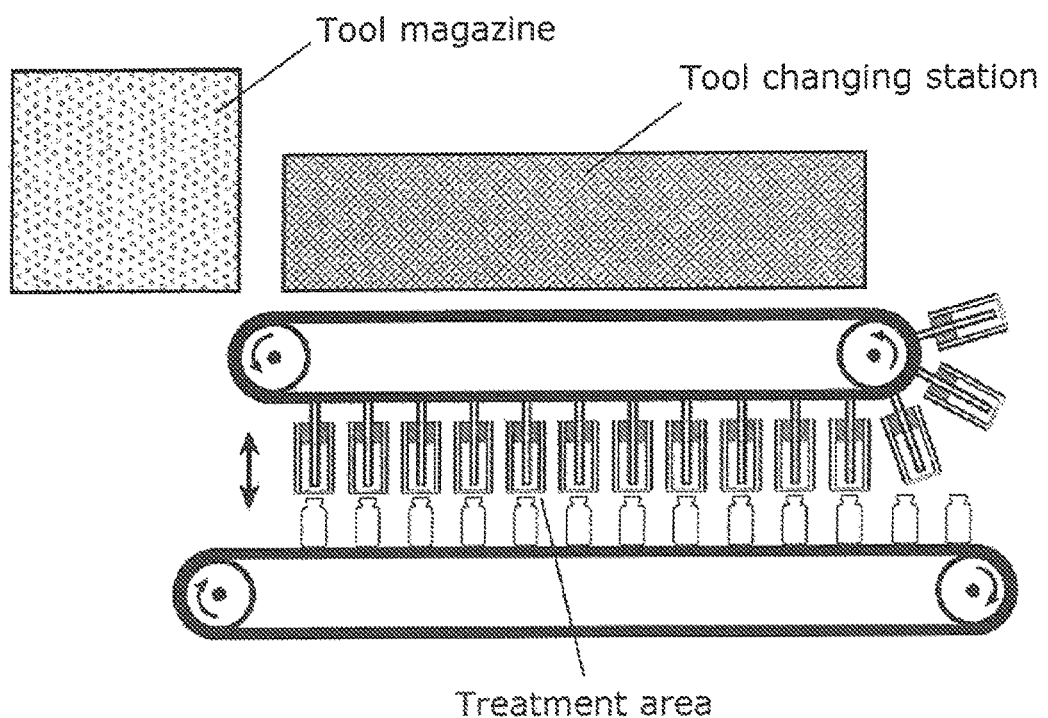

The device according to a preferred embodiment of the invention is shown schematically in FIGS. 1, 2 and 3.

According to FIGS. 1 to 3, the device has an electrically conductive internal tube [1], via which gases can be discharged or supplied. For this, openings in the tube, e.g. at position [2], are used. The internal tube [1] can serve as an internal electrode of a dielectric barrier discharge or as a coaxial internal conductor of a high-frequency or microwave supply. For this, it can also be provided with special structures in order to ensure a better ignition of the plasma. The internal tube can be covered with a dielectric for additional insulation or for increasing the chemical durability. The internal tube is galvanically insulated—preferably by a flange [3]—connected with two external tubes [4, 6]. At least one of them is electrically conductive. The two tubes can be at the same potential. It is particularly advantageous to set it on earth potential. Dielectric casings can also be used here. The tube [6] can also be used as a further dielectric. The electrically conductive external tube(s) then form the second electrode in the case of the operation as dielectric barrier discharge. In the case of a high-frequency or microwave excitation of the plasma, it represents the coaxial external conductor. Furthermore, the dielectric required for a dielectric barrier discharge can also be represented by the object to be treated itself.

The device is pushed for treatment over the object to be treated (see FIGS. 4 and 5) and the external tube [4] contacts the preferably earthed base plate [8]. The most gas-impermeable connection possible is produced by a seal in [5].

Through a supply of the working gases through the openings [9] and exhaust of the gases through the openings [2] in the internal tube, a slight overpressure can be achieved at a corresponding gap width between [6] and [8] in the corresponding gas flow in the gap between [4] and [6]. In contrast, normal pressure to underpressure prevails in the treatment area between [6] and [1]. It is achieved through this operating method that the requirements of the sealing system [5, 7] are not high. If this seal fails, it does not lead to a contamination of the process gas and thus an accompanying process outage. The consequence of a seal failure is primarily the increased gas consumption, which is easy to detect and can be fixed.

In order to achieve an improved adjustment of the pressure ratios in the intermediate space between [4] and [6] and the treatment chamber between [1] and [6], the gap dimension from [6] to [8] can be varied. An additional seal can also be installed for example in [6], and the gas supply can be achieved via bore holes through the walls. These can be regulated for example in that [6] is designed as two parts and the bore holes can be opened or respectively closed by twisting the two concentric tubes against each other.

The method and device are thus particularly suitable for a high number of load cycles.

For flushing, e.g. to remove toxic gases forming in the process, the gas flow as well as the pressure areas can be reversed.

Additionally, a tangential gas flow can be created, which leads to a centring of the object to be treated, through additional gas channels in [6] or respectively sloping grooves in the floor of [6] between [6] and the object to be treated. Through an increase in the flow speed, a lifting of the object to be treated from the floor plate can be achieved, and a treatment of the outer floor area of the object to be treated can thus also be achieved.

Another option for lifting the object to be treated from the floor plate [8] can be achieved when the internal tube [1] or respectively parts of it can move in the case of a two-part design in relationship to the external tubes [4] and [6] such that the floor of the bottom can be suctioned via a corresponding device and the treatment product can then thus be lifted so that the bottom side can be treated.

A sealing effect between the object to be treated and the flange [3] can also be achieved through this method in the case of bottles and hollow bodies, which leads to a pressure gradient between the interior and exterior of the object to be treated and can be advantageously used for process control and plasma formation.

The invention claimed is:

1. A device for plasma-treating hollow bodies (10), comprising a base plate (8), an electrically conductive internal tube (1) and, two external tubes (4, 6), namely an inner external tube (6) and an outer external tube (4), of which
   at least the inner external tube (6) or the outer external tube (4) is electrically conductive,
   wherein the inner external tube (6) and the outer external tube (4) are connected to each other so as to be impermeable to gas, such that an antechamber between the two external tubes (4, 6) is formed;
   a plasma generating device for generating a plasma between the internal tube (1) and the inner external tube (6);
   and a flange (3) between the internal tube (1) and the inner external tube (6), configured to form a treatment chamber between the inner external tube (6) and the internal tube (1);
   wherein the internal tube (1) and the inner external tube (6) are galvanically insulated from each other by the flange (3);
   and wherein the outer external tube (4) is connected or is connectable with the base plate (8) via a seal (5) and the inner external tube (6) is connected or is connectable with the base plate (8) via an adjustable contact seal (7).

2. The device according to claim 1, wherein the interior tube (1) has at least one opening (2) and the antechamber has at least one opening (9) for filling in or suctioning out gases.

3. The device according to claim 1, wherein the two external tubes (4, 6) and the base plate (8) are at a same potential.

4. The device according to claim 1, wherein the internal tube (1) and the two external tubes (4, 6) are arranged concentrically.

5. The device according to claim 1, wherein the internal tube functions as a high-voltage electrode in the case of a dielectric barrier discharge and is covered with a dielectric.

6. The device according to claim 1, wherein the inner external tube (6) serves as a dielectric.

7. The device according to claim 1, wherein the inner external tube (6) is designed as two parts and/or contains additional openings for gases and/or an additional seal.

8. The device according to claim 1, wherein the inner external tube (6) has additional gas channels and respectively sloping grooves in the base plate (8).

9. A beam system, comprising a plurality of devices, wherein each device from the plurality of devices is a device according to claim 1, wherein said plurality of devices are combined into beams, which can be moved along in parallel with a transport of vials by means of transport chains arranged for transporting the vials and said plurality of devices.

* * * * *